United States Patent [19]

Gatling

[11] 4,237,303

[45] Dec. 2, 1980

[54] REMOVAL OF OXAZOLE FROM ACRYLONITRILE

[75] Inventor: Sterling C. Gatling, Bay City, Mich.

[73] Assignee: The Dow Chemical Company, Midland, Mich.

[21] Appl. No.: 34,892

[22] Filed: Apr. 30, 1979

Related U.S. Application Data

[63] Continuation-in-part of Ser. No. 922,630, Jul. 5, 1978, abandoned.

[51] Int. Cl.³ ................. C07D 263/32; C07C 121/32
[52] U.S. Cl. ................................ 548/235; 260/465.3; 260/465.9
[58] Field of Search ............ 260/307 R, 465.3, 465.9; 548/235

[56] References Cited

U.S. PATENT DOCUMENTS

| | | | |
|---|---|---|---|
| 2,609,387 | 9/1952 | Basdekis et al. | 560/218 |
| 3,541,131 | 11/1970 | Darcas et al. | 260/307 R |
| 3,574,687 | 4/1971 | Darcas et al. | 260/307 R |
| 3,969,344 | 7/1976 | Ackermann et al. | 260/340.7 |

*Primary Examiner*—Jose Tovar
*Attorney, Agent, or Firm*—Gary R. Plotecher; Charles J. Enright

[57] ABSTRACT

A process for the removal of oxazole from acrylonitrile by contacting oxazole-containing acrylonitrile with a substantially dry cation exchange resin. The process exhibits the advantage of up to 40 percent or greater increase in the oxazole removal capacity than a corresponding process employing a water-wet cation exchange resin.

15 Claims, No Drawings

REMOVAL OF OXAZOLE FROM ACRYLONITRILE

CROSS REFERENCE TO RELATED APPLICATION

This is a continuation-in-part of copending application Ser. No. 922,630, filed July 5, 1978, now abandoned.

BACKGROUND OF THE INVENTION

The present invention relates to a process for removing oxazole impurity from acrylonitrile. The oxazole impurity is commonly formed in the widely used process for production of acrylonitrile by amoxidation of propylene. Acrylonitrile prepared by the invention is useful for the preparation of high quality acrylonitrile polymers or as feed for a catalytic hydration process of acrylonitrile to acrylamide.

In U.S. Pat. Nos. 3,541,131 and 3,574,687, oxazole is removed from acrylonitrile prepared by the amoxidation of propylene. Acrylonitrile containing about 0.3 weight percent water and about 85 ppm oxazole therein is purified by contacting with a water-wet cation exchange resin in the acid form and regenerated with deionized water. U.K. Pat. No. 1,131,134 teaches that oxazole may be removed from acrylonitrile by hydroextractive distillation and U.S. Pat. No. 3,969,344 teaches the purification of polymerizable monomers, acrylonitrile is mentioned, over a porous cation exchange resin of certain pore size and specific surface area which is in the form of the alkali or alkaline earth metal salt thereof. The removal of amine polymerization inhibitors from unsaturated monomers is described in U.S. Pat. No. 2,609,387 by contact with an alcohol dried cation exchange resin in the hydrogen form. The specific examples of monomers so treated are styrene and methyl acrylate while nitriles of acrylic acid are generically described as so treatable. However, the technology for amoxidation of propylene to acrylonitrile was not commercially developed at the time of this teaching and oxazole is not there mentioned as an amine polymerization inhibitor for such monomers.

Other U.S. patents mention purification of acrylonitrile containing methyl vinyl ketone impurities by contact with either cation or anion exchange resins: U.S. Pat. Nos. 3,146,258 and 2,792,415; others mention purification of acrylonitrile with ion exchange resins in conjunction with neutral decolorizing agents such as charcoal beds: U.S. Pat. Nos. 2,444,589 and 2,622,097. The latter of these indicates that water must be added from time to time to rehydrate the beds for effective operation. U.S. Pat. Nos. 2,351,157 and 2,770,645 relate to solution treatments of acrylonitrile to remove impurities therefrom.

SUMMARY OF THE INVENTION

The invention is a process for the removal of oxazole from oxazole-containing acrylonitrile comprising contacting the acrylonitrile with a cation exchange resin which contains less than about the amount of water contained in a water-moist commercial cation exchange resin under standard conditions prior to contact with the acrylonitrile. Under standard conditions, 25° C. and 760 mm Hg, commercially available water-moist cation exchange resins commonly contain about 40–50 percent water, combined weight by Karl-Fischer analysis. Preferably, the water content of the resin is less than about 35 weight percent based on the combined weight of water and resin, more preferably less than 25 weight percent and most preferably less than 15 weight percent prior to contact with the acrylonitrile to be purified.

The water content of the oxazole-containing acrylonitrile is initially less than about the saturation point for water in acrylonitrile at the temperature of the solution. At about 25° C., this will amount to less than about 6 percent water (60,000 ppm) based on the weight of acrylonitrile. Preferably, the acrylonitrile to be treated will initially contain less than about 1 percent water (10,000 ppm), more preferably less than about 0.1 percent water (1,000 ppm) and most preferably less than about 0.05 percent water (500 ppm), based on the weight of the acrylonitrile.

At least a portion of the cation exchange resin is in the acid form, and preferably is primarily in the acid form, prior to contact with the acrylonitrile. Preferably the resin is a sulfonated poly(vinylaromatic) resin. More preferably, the resin is a sulfonated cross-linked polystyrene resin, most preferably primarily in the acid form.

The process may be carried out at any convenient temperature but is preferably carried out at temperatures below about 50° C. since increases in temperature above that level tend to decrease the capacity of the resin for oxazole. The process is conveniently carried out at the ambient temperature of its surroundings and preferably is carried out at a temperature not less than 0° C. since it is inconvenient to cool the acrylonitrile and apparatus below that temperature. Operation at a temperature of between about 0° C. and about 50° C. is preferred.

Once breakthrough of oxazole in the product from the process is noted, or earlier, regeneration may be undertaken. Oxazole is removed from the resin by contacting with methanol or water, with a regeneration preference for aqueous systems having a pH of less than 7, more preferably less than 6. Oxazole may also be stripped from the resin by passing steam through it. Generally, heating the resin bed or the regenerant or both tends to increase the speed and efficiency of regeneration.

DETAILED DESCRIPTION OF THE INVENTION

The cation exchange resin to be employed in the process may be any of a number of commercially available cation exchange resins, either gel or macroporous type. The resin is preferably employed primarily in its acid form although a portion of the other ion exchanging sites may be converted to the form of ammonium salts or other salts. However, this lowers the capacity of the resin and is not preferred. The cation exchange resin can be mixed with anion exchange resin but this merely increases the volume of the apparatus necessary to attain a given capacity and is therefore not generally desirable. Preferred are strong acid cation exchange resins, i.e., those containing phosphoric acid groups or more preferably, sulfonic acid groups. While various phenolic cation exchange resins exist, a poly(vinylaromatic) resin backbone is preferred, more preferably a cross-linked polystyrene, that is a polystyrene which contains up to about 10 percent divinylbenzene as a cross-linker. Most commercially available strong acid resins are polystyrenes, containing 4 to 8 percent divinylbenzene, which have been sulfonated to contain about one sulfonic group per aromatic ring. Standard commercially available cation exchange resins in bead form and of readily available mesh size are suitable for use in the invention. Generally particles of about 20–200 mesh (U.S. Sieve) are suitable but smaller or larger particles may be employed.

The cation exchange resin is suitably dried by heating to a temperature between about 50° C. and 100° C. and simultaneously passing dry nitrogen or air through the resin. Since it is convenient to utilize the resin in the form of a bed packed in a cylindrical column or pipe, the bed may be heated externally and the dry gas stream passed upward through the bed. Wet resin may be dried solely by application of heat for an extended period of time but care must be taken to avoid degrading the resin since most commercially available resins begin to thermally degrade or lose their effectiveness when exposed to temperatures in excess of about 125° C. Suitably, the resin is dried at about 60° C. by passing a stream of dry nitrogen through a resin bed at a rate of about 2000 bed volumes per hour for about 30 to 60 minutes.

Commercial acrylonitrile prepared by the amoxidation of propylene is commonly available with an oxazole content of 200 to 300 ppm. Preferably, one employs in the process acrylonitrile containing the lowest amount of water possible in order to extend the effective life of the resin before regeneration is necessary. If low water content acrylonitrile is not available, it is preferable to dry the acrylonitrile to less than about 1 percent water by fractional distillation at low temperatures under vacuum or by passing it first over a bed of suitable desiccant such as calcium chloride.

While the majority of commercial acrylonitrile is prepared by amoxidation of propylene, acrylonitrile may also be produced by amoxidation of acrolein or other older methods. The method by which the acrylonitrile is prepared is not critical to the present purification process since not the source but the presence or absence of the oxazole impurity is the determinative factor. While it would generally be desirable to purify according to the present process, acrylonitrile having minimal initial oxazole content, the process may be used to remove larger amounts of oxazole. To do so, one merely increases proportionally the amount of resin contacted with the acrylonitrile to be purified. Preferably, the acrylonitrile purified by the present process initially contains less than about 1000 ppm oxazole, more preferably less than about 500 ppm oxazole and most preferably less than about 200 ppm oxazole, based on the weight of acrylonitrile.

Preferably, acrylonitrile treated in accordance with the present invention will contain less than about 20 ppm oxazole, more preferably less than about 5 ppm oxazole and most preferably less than about 2 ppm oxazole, based on the weight of acrylonitrile, after decontacting from the resin. Generally, when oxazole content of the acrylonitrile purified by the present process rises to a level of about 20–50 ppm, the cation exchange resin's capacity should be considered exhausted and the resin may then be regenerated.

Flow rate of acrylonitrile in the process is not critical and may range from about 10 to 150 bed volumes per hour. The capacity of the resin for removal of oxazole is found to be better at the lower flow rates on the order of about 25 bed volumes per hour.

The process may be carried out as a batch process or as a continuous process. Because the cation exchange resin may be immobilized by packing in a column, a continuous process can be operated; such a mode of operation is convenient and preferred. The length to diameter ratio of such a packed bed is not critical if well packed and several times unity in the length to diameter ratio is sufficient, a ratio of 5 up to about 50 being operable.

The temperature of the process is not critical and ambient temperature is suitable for operation. However, it has been noted that the capacity of the resin for oxazole removal is inversely proportional to temperature. However, between the temperatures of about 0° C. and 50° C. the capacity of such a resin is quite good.

One regenerates the resin, if desired, suitably by contacting it with water, preferably at a pH less than 7, more preferably less than about 6. It has been found that regeneration is more efficient at elevated temperatures and is preferably carried out at a temperature between about 75° C. and 125° C. It is preferred to use steam alone to strip oxazole from the resin and low pressure, 100° C. steam forced through the oxazole-containing resin bed works admirably. The regenerant, containing oxazole, may be recovered and oxazole separated therefrom by any standard means or may be disposed of as desired. After regeneration, the resin is redried as previously described.

SPECIFIC EMBODIMENTS

In the following examples a 250 mm glass column of 6 mm internal diameter, equipped with a steam jacket, is packed with a strong acid cation exchange resin on a glass wool support. Acrylonitrile is pumped down through the packed column. Oxazole content is determined by gas chromatography, lower limit of detection about 20 ppm oxazole, based on the weight of acrylonitrile as reported herein. However, by extracting oxazole from a sample with a cation resin, recovering the oxazole from the resin by washing with hot water and then analyzing the recovered aqueous oxazole sample by gas chromatography the interference of acrylonitrile with oxazole determinations at levels less than 20 ppm may be avoided. In this fashion, oxazole levels of less than 1 ppm may be measured.

The cation exchange resins employed are about 100–200 mesh (U.S. Sieve) DOWEX HCR-W2 strong acid cation resin, a gel type resin, and about 20–50 mesh DOWEX MSC-1 strong acid cation resin, a macroporous type resin, both marketed by The Dow Chemical Company. The resins as obtained are water-moist. They are dried by heating for about 12–15 hours at about 100° C. under a vacuum of about 25 mm Hg or by passing dry nitrogen through the resin bed for about 45 minutes at about 60° C.–65° C. By controlling the nitrogen flow rate, the degree of dryness is varied. Water content is determined by Karl-Fischer titration.

EXAMPLE 1

Water Content of Resin

Water-moist DOWEX MSC-1 resin in the acid form is loaded in a column. The water content is about 47 percent, based on the combined weight of the resin and water. A stream of acrylonitrile containing about 900 ppm water, based on acrylonitrile weight, is passed through the column at about 25° C. After about 190 bed volumes have passed through the column, the water content of the resin is found to be about 11 weight percent. Similarly, a stream of acrylonitrile containing about 3000 ppm water is passed through a bed of the water-moist (47 percent) resin at 25° C. After about 20–25 bed volumes, the water content of the resin is about 23 weight percent. Using 7000 ppm water-containing acrylonitrile, after about 280 bed volumes, the water content of the originally water-moist resin drops to about 11 weight percent. This shows that the resin may be dried with low water content acrylonitrile and will place the resin in suitable form for use. The capacity of the resin will remain high if the oxazole content of the acrylonitrile used to dry is low, i.e., less than 50 ppm, preferably less than 20 ppm. This suggests that one may pass the low water (<3000 ppm) and low oxazole eluent from the instant process to a second water-moist resin column to dry the second column and thereby avoid the need to dry with nitrogen or heat. The results of this example are represented in the following Table I.

TABLE I

| Acrylonitrile Water Content | Bed Volumes Passed | % Water Content of Resin |
|---|---|---|
| — | None | 47 |
| 900 ppm | 190 | 11 |
| 3000 ppm | 20–25 | 23 |
| 7000 ppm | 280 | 11 |

A sample of DOWEX HCR-W2 resin in the acid form is dried under vacuum at 100° C. as previously described. The water content is ultimately about 10 weight percent. Likewise, a DOWEX MSC-1 resin sample is dried. The ultimate water content is about 9 weight percent. Samples of DOWEX MSC-1 resin are also dried, as previously described, with dry nitrogen at about 60° C.–65° C., varying the amount of nitrogen passed through the resin, to give dried resin samples with water content of about 5 to 17 weight percent.

EXAMPLES 2–6

Column Runs

Samples of wet and dried resin, previously described, are placed in the 250×6 mm column and a stream of acrylonitrile containing about 163 ppm oxazole and varying water content is passed through the resin, with samples of effluent being analyzed for oxazole content at about 100 cc intervals. Breakthrough of oxazole at about 40–50 ppm is noted and resin capacity calculated at breakthrough point for the particular resin. The performance of the various resin samples as a function of water content of resin and acrylonitrile is described in Table II.

TABLE II

| Ex. | Resin | Water Content of Resin (Wt. %) | Water Content of Acrylonitrile (ppm) | Oxazole Capacity of Resin (kg/m³) |
|---|---|---|---|---|
| 2 | DOWEX HCR-W2 (H⁺ form) | 10 | 3000 | 36.8 |
| 3 | DOWEX MSC-1 (H⁺ form) | 47 | 3000 | 23.5 |
| 4 | DOWEX MSC-1 (H⁺ form) | 5 | 3000 | 35.2 |
| 5 | DOWEX MSC-1 (H⁺ form) | 47 | 15000 | <13.1 |
| 6 | DOWEX MSC-1 (H⁺ form) | 5 | 15000 | 20.3 |

EXAMPLES 7 and 9

Batch Runs

Weighed samples of DOWEX MSC-1 resin (H+form) of varied water content are slurried with acrylonitrile containing 900 ppm water and 163 ppm oxazole. The slurries are vigorously shaken, the resin settles out, an aliquot of the supernatant acrylonitrile is taken and oxazole content of the acrylonitrile is measured. By difference, the oxazole content of the resin is determined and from this, the capacity of the resins for oxazole is calculated and reported in Table III.

TABLE III

| Example | Water Content of Resin (Wt. %) | Oxazole Capacity of Resin (kg/m³) |
|---|---|---|
| 7 | 47 | 6.1 |
| 9 | 5 | 13.6 |

EXAMPLES 10–14

Regeneration

Samples of DOWEX MSC-1 resin which have been saturated with oxazole are regenerated by passing deionized (DI) water, steam, 1 N aqueous sulfuric acid and methanol through the resin bed. The weight ratio of regenerant required per unit of oxazole recovered from the resin for varied conditions is reported in Table IV.

TABLE IV

| Example | Regenerant | Temperature (°C.) | Regenerant/Oxazole (Wt Ratio) |
|---|---|---|---|
| 10 | DI H₂O | 25 | 550 |
| 11 | DI H₂O | 60 | 135 |
| 12 | Steam | 100 | 80 |
| 13 | Methanol | 100 | 3000 |
| 14 | 1N H₂SO₄ | 25 | 280 |

What is claimed is:

1. A process for removal of oxazole from oxazole-containing acrylonitrile comprising contacting the acrylonitrile with a cation exchange resin which resin prior to contact with the acrylonitrile, contains less than about 40 percent water based on the combined weight or resin and water and at least a portion of which resin is in the acid form.

2. The process of claim 1 wherein the water content of said cation exchange resin prior to contact with the acrylonitrile is less than about 35 percent based on the combined weight of the resin and water.

3. The process of claim 1 wherein the water content of the acrylonitrile is less than about 6 percent based on the weight of acrylonitrile.

4. The process of claim 1 wherein the resin is a sulfonated poly(vinylaromatic) resin.

5. The process of claim 4 wherein the resin is primarily in the acid form prior to contact with the acrylonitrile.

6. The process of claim 1 wherein the resin is a sulfonated cross-linked polystyrene.

7. The process of claim 6 wherein the resin is primarily in the acid form.

8. The process of claim 7 wherein the water content of the cation exchange resin prior to contact with the acrylonitrile is less than about 15 percent based on the combined weight of the resin and water.

9. The process of claim 8 wherein the water content of the acrylonitrile is less than about 0.1 percent based on the weight of acrylonitrile.

10. The process of claim 1 wherein the acrylonitrile and the resin are contacted at a temperature of between about 0° C. and about 50° C.

11. The process of claim 1 wherein the resin has previously had water removed by contacting with a prior acrylonitrile containing less than about 50 ppm oxazole and less than about 3000 ppm water, based on the weight of said prior acrylonitrile.

12. The process of claim 11 wherein said prior acrylonitrile contains less than about 20 ppm oxazole and less than about 1000 ppm water.

13. The process of claim 1 wherein the water content of the acrylonitrile is less than about 1 percent, based on the weight of acrylonitrile.

14. The process of claim 1 wherein the acrylonitrile is derived from the amoxidation of propylene.

15. The process of claim 1 wherein the acrylonitrile so treated, after decontacting from the resin, contains less than about 20 ppm oxazole based on the weight of acrylonitrile.

* * * * *